United States Patent [19]

Feld

[11] 3,950,642

[45] Apr. 13, 1976

[54] METHOD OF INSPECTING SHOT PEENED SURFACES FOR EXTENT OF COVERAGE

[75] Inventor: Paul G. Feld, La Mirada, Calif.

[73] Assignee: Metal Improvement Company, Inc., Teanech, N.J.

[22] Filed: May 27, 1975

[21] Appl. No.: 581,211

[52] U.S. Cl. .................... 250/302; 51/320; 73/88 R
[51] Int. Cl.² .................................................. G09K 3/00
[58] Field of Search ...... 250/302, 361; 73/11, 88 A, 73/88 R, 104, 105; 51/319, 320, 321

[56] References Cited
UNITED STATES PATENTS

| | | | |
|---|---|---|---|
| 2,920,203 | 1/1960 | Switzer | 250/302 |
| 3,695,091 | 10/1972 | Smith | 73/88 R |

*Primary Examiner*—Harold A. Dixon
*Attorney, Agent, or Firm*—Arthur Frederick; Victor D. Behn

[57] ABSTRACT

The method of inspecting shot peened surfaces of a workpiece for the extent of coverage comprises coating the surface to be peened of a workpiece with a material containing a fluorescent dye and then shot peening the part to be peened until the amount of fluorescent coating remaining, as indicated by the amount of fluorescent radiation given off when exposed to ultraviolet light, compares with the amount of fluorescent radiation given off from a previously prepared control specimen which has the same material characteristics as the workpiece and was coated with the same fluorescent material and shot peened to a desired coverage.

10 Claims, 1 Drawing Figure

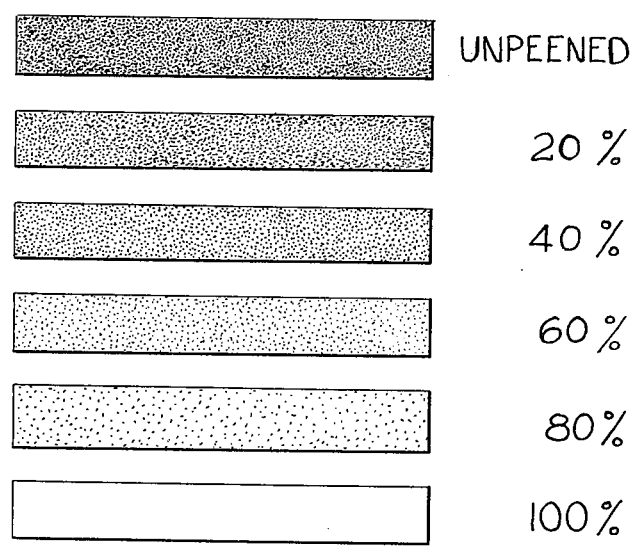

METHOD OF INSPECTING SHOT PEENED SURFACES FOR EXTENT OF COVERAGE

This invention relates to surface treatment of metallic workpieces by shot peening and, more particularly, to a method of inspecting shot peened surfaces of workpieces for the extent of coverage.

It is well known that by bombarding the surface of a metal part with metal or glass beads (the process being referred to as "shot peening"), a compressive layer is produced in the metallic surface whereby increased fatigue strength and resistance to stress corrosion is imparted to the workpiece. Also, shot peening has been employed to bend metallic members into predetermined configurations which cannot be produced by other practicable methods.

In performing shot peening operations it is difficult to obtain uniform intensity of peening and the desired extent of coverage on parts, particularly those parts having intricate shapes. Where shot peening is being performed essentially for prevention or minimization of stress corrosion, the extent of coverage over the surface to be peened is of particular concern to insure that the compressive layer extends over the entire surface to be treated. The degree of peening intensity is conventionally measured in the Almen Scale by use of an Almen test strip. This method of gaging or measuring peening intensity is fully disclosed in an article by H. F. Moore entitled, "Shot Peening and The Fatigue of Metals", published by the American Foundry Equipment Co. and the U.S. Pat. No. 3,695,091, to Smith, dated Oct. 3, 1972. Thus, with a practical way of measuring intensity of peening, there only remains the problem of assuring that the surface to be peened has been covered to the desired extent. Not only is the extent of peening coverage important where peening is being performed to minimize stress corrosion, but it is important where shot peening is performed essentially for the improvement of fatigue strength and/or prevention of fatigue failure. In this situation, the extent of coverage over critical areas of stress concentration is of particular concern to insure that the compressive layer extends without interruption over the entire surface to be treated. Present methods require visual inspection under at least ten-power magnification, thus leaving the question of extent of peening coverage to the "trained eye" and judgement of an expert. To compound the problem, it is extremely difficult, if not at times impossible, to visually examine large peened surface areas with a magnifying glass of ten-power which is required by some military specifications and aircraft manufacturers.

Accordingly, it is an object of this invention to provide a method of inspecting shot peened surfaces of workpieces to determine the extent of the peening coverage, which method is relatively simple, inexpensive and accurate.

It is another object of the present invention to provide a method of inspecting shot peened surfaces of workpieces to insure complete peening coverage of the surfaces, which method has application to intricately shaped workpieces.

A further object of this invention is to provide a method of inspecting shot peened surfaces for completeness of coverage which does not require the judgement of an expert in the shot peening art.

SUMMARY OF THE INVENTION

The present invention therefore contemplates a method of inspecting shot peened surfaces of workpieces to determine the extent of shot peening coverage which comprises the hereinafter set forth steps.

The surface of a control specimen, or strip composed of like material as the workpiece or part to be shot peened, is coated with an identifiable material. The surfaces of a workpiece or part to be peened is coated with the same identifiable material used to coat the control specimen.

The surface of the control specimen having the coating of identifiable material is subjected to shot peening until the desired peening coverage has been obtained as indicated by the change in the appearance of the coating on the peened surface. This control specimen, after peening, may be visually inspected under magnification to attain a still more accurate determination of the extent of coverage and, therefore, its appearance.

The surfaces of the workpiece to be peened are shot peened so that, in the process, portions of the identifiable coating material is removed. Thereafter, the shot peened surfaces of the workpiece are compared with the peened surface of the control specimen. If the compared surfaces of the workpiece and control specimen appear to be the same, the shot peened surface of the workpiece is then known to have received the desired extent of peening coverage. If the appearance of the compared surfaces are not the same, then the workpiece is further shot peened until the compared surfaces are substantially identical in appearance.

In a more narrow aspect of this invention, the identifiable material is a liquid containing a dye. The dye is preferably one which has a luminescent property which is responsive to light. Still more specifically, the dye may be soluble in a liquid vehicle or carrier and which dye is relatively unstable when exposed to ultra-violet light. Many possible suitable materials for metallic workpieces of various characteristics are disclosed in the U.S. Pat. Nos. 2,259,400, to Switzer, dated Oct. 14, 1941 and de Forest et al, 2,774,886, dated Dec. 18, 1956. A standard fluorescent ink, No. 220, has proven suitable for very hard metallic parts, such as steel having a hardness of 260–280 KSI. The liquid containing dye may be brushed or sprayed on the workpiece and control specimen or the members dipped into a bath of such liquid. After application, the liquid is allowed to dry or set-up before shot peening.

In a still narrower scope of the present invention, the surfaces of the workpiece and control specimen or strip which are to be peened are coated with a liquid containing a fluorescent dye. The control specimen is shot peened to the extent deemed necessary to provide on the workpiece a surface that has optimum fatigue strength or resistance to stress corrosion. Thereafter, the shot peened surface of the control specimen may then be examined for the extent of coverage by an expert, under ultra-violet light, including, if desired, examination under ten-power magnification. The workpiece surfaces are then shot peened and compared under exposure to ultra-violet light to determine whether or not the fluorescent radiation from the peened surfaces matches that of the control specimen. Obviously, this latter comparison need not be performed by an expert in the peening art. If the fluorescent radiation of the workpiece does not match that of the control specimen, further peening is performed until a comparison, as aforesaid, establishes that the extent of coverage on the workpiece matches that on the control specimen.

BRIEF DESCRIPTION OF THE DRAWINGS

The invention will be more fully understood from the following description thereof when considered with the accompanying drawing in which is illustrated six test control specimens showing different extents of peening coverage under ultra-violet light.

DESCRIPTION OF THE PREFERRED EMBODIMENTS

The method, according to this invention, of inspecting shot peened surfaces of a part or workpiece to determine the extent of shot peening coverage to insure that the part has optimum fatigue strength or resistance to stress corrosion is as herein set forth.

Initially, a control specimen or strip, such as depicted in the drawing, is coated with a material, preferably consisting of a carrier liquid such as a resin-based compound which drys reasonably rapidly and contains a fluorescent dye which is relatively unstable under exposure to ultra-violet light. Of course, any other suitable material, capable under any type of light of rendering visible different accumulations of color on the peened surface, may be employed. Various other coating materials may be usable in association with workpieces of various metals and compositions. Many potentially suitable coating materials are disclosed in the U.S. Pat. Nos. 2,259,400, to Switzer, dated Oct. 14, 1941; de Forest et al, 2,774,886, dated Dec. 18, 1956; Thornbury, 3,108,187, dated Oct. 22, 1963 and Geib, 3,675,015, dated July 4, 1972. The control specimen is selected from the same material of which the workpiece or part to be peened is composed, or from a material having substantially the same characteristics, such as hardness and porosity. One such coating material found to be suitable on very hard metallic workpieces such as steels having a hardness of 260 to 280 KSI, is the standard fluorescent ink, No. 220.

After the control specimen has been applied with a coating material by any suitable means such as brushing or spraying or dipping, the strip in a bath of coating material, it is allowed to dry or set-up. The coated surface is then inspected to insure completeness of the coating. The control specimen is then shot peened in the process of which some coating material is removed. The shot peened control specimen is periodically inspected by a person skilled in the shot peening art to determine when the control specimen has been treated to provide the extent of coverage desired. As illustrated in the drawing, the extent of coverage is measured by the amount of coating removed from the surface by the shot peening process. To insure a high degree of accuracy in determining the extent of coverage, as for example 100% coverage, and comply with customer specifications, the control specimen may be examined under magnification. In most specifications, the magnification required would be in the order of ten-power. By this process a control specimen is produced which, in accordance with this invention, is used in connection with determining the extent of peening coverage on a workpiece as hereinafter more fully described.

The surfaces of a workpiece or part to be peened are coated with the same coating material employed in producing the control specimen. After application of the coating material it is allowed to dry or set-up and the workpiece is then inspected to insure that all of the surfaces to be peened have been coated with the coating material. In the case of coating material containing a fluorescent composition, agent or dye, the inspection is preferably conducted under exposure to ultra-violet light.

Thereafter, the workpiece surfaces to be peened are shot peened to a predetermined intensity as measured under the Almen Scale, the workpiece is examined in relation to the control specimen to determine whether or not the required coverage has been obtained. In the case where the coating material contains a fluorescent composition, agent or dye, the comparison examination is made by exposing the workpiece to ultra-violet light. If the fluorescent radiation in all areas of the surfaces to be peened on the workpiece matches that of the fluorescent radiation emitted by the control specimen under ultra-violet light, the workpiece has then been given the desired peening coverage. If such comparison examination indicates certain areas of the surfaces to be peened of the workpiece have not received shot peening or have received insufficient shot peening, those areas are then shot peened and a further comparison examination is made to insure that the desired coverage has been achieved.

It is believed now readily apparent that the present invention provides a method of inspecting shot peened surfaces of a workpiece to determine the extent of shot peening coverage which, in the field or in the production line, can be reliably performed by relatively unskilled persons. It is a method which is suitable for insuring desired shot peening coverage on intricately shaped workpieces. The method also is relatively inexpensive, accurate and reliable.

Although but one embodiment of the invention has been described in detail, it is to be expressly understood that the invention is not limited thereto. Various changes can be made in the method steps without departing from the scope and spirit of the invention as the same will now be understood by those skilled in the art.

What is claimed is:

1. The method of inspecting shot peened surfaces of a workpiece to determine the extent of shot peening coverage comprising the steps of:
   a. providing a control specimen composed of like material as the part to be shot peened with a coating of identifiable material;
   b. shot peening the control specimen until a predetermined peening coverage has been obtained as indicated by the change in the appearance of the coating on the peened surface;
   c. shot peening the surface of the workpiece to be peened which surface has been coated with the same identifiable material as the control specimen; and
   d. comparing the appearance of the shot peened surface of the workpiece with the appearance of the control specimen so that when the compared surfaces are the same in appearance, the shot peened surface of the workpiece is known to have been subjected to said predetermined peening coverage.

2. The method of claim 1 wherein the workpiece to be peened before shot peening is inspected to insure that the entire surface to be peened has been coated with said identifiable material.

3. The method of claim 1 wherein said identifiable material is a liquid containing a dye.

4. The method of claim 1 wherein said identifiable material is a liquid containing a dye which has a luminescent property responsive to light.

5. The method of claim 4 wherein said dye becomes vividly fluorescent during exposure to fluorescigenous radiant energy so that the step of comparing the control specimen shot peened surface and shot peened surface of the workpiece includes exposure of such surface to fluorescigenous radiant energy.

6. The method of claim 1 wherein the shot peened surface of the control specimen is examined for the extent of peening coverage under magnification.

7. The method of claim 6 wherein magnification is about ten-power.

8. The method of inspecting a shot peened surface of a workpiece to determine the extent of shot peening coverage comprising the steps of:
   a. selecting a control specimen of a material having the same characteristics as the material of the workpiece to be peened and coating the control specimen and the surfaces of the workpiece with a material containing a fluorescent dye;
   b. shot peening the control specimen until the desired peening coverage has been obtained by examination of the surface under magnification and as indicated by the degree of radiation emitted by the surface when exposed to ultra-violet light;
   c. shot peening the surface of the workpiece to be peened; and
   d. comparing the appearance of the peened surfaces of the workpiece to be peened under ultra-violet light with the appearance of the control specimen under ultra-violet light and further shot peening the workpiece when necessary until the appearance of all the areas of the peened surfaces of the workpiece match the appearance of the control specimen.

9. The method of claim 8 wherein said control specimen and workpiece to be peened are hard steels and the dye is fluorescent ink, No. 220.

10. The method of claim 8 wherein the workpiece before shot peening is subjected to ultra-violet light to insure that the entire surfaces to be peened have been coated with the liquid containing the fluorescent dye.

* * * * *